United States Patent [19]

Schwartz et al.

[11] Patent Number: 5,225,585
[45] Date of Patent: Jul. 6, 1993

[54] PRODUCTION OF FLUOXETINE AND NEW INTERMEDIATES

[75] Inventors: Eduard Schwartz, Rehovot; Joseph Kaspi, Givataim; Zinovi Itov, Rishon-Lezion; Gidon Pilarski, Holon, all of Israel

[73] Assignee: Teva Pharmaceutical Industries Ltd., Jerusalem, Israel

[21] Appl. No.: 931,312

[22] Filed: Aug. 18, 1992

[30] Foreign Application Priority Data

Aug. 27, 1991 [IL] Israel .......................... 99316

[51] Int. Cl.[5] .................. C07C 209/08; C07C 271/22
[52] U.S. Cl. ...................... 558/275; 564/347
[58] Field of Search .......... 558/275; 564/347

[56] References Cited

U.S. PATENT DOCUMENTS

| | | | |
|---|---|---|---|
| 4,018,895 | 4/1977 | Molloy et al. | 564/342 X |
| 4,194,009 | 3/1980 | Molloy et al. | 564/347 X |
| 4,199,004 | 4/1980 | Wada et al. | 137/493 |
| 4,314,081 | 2/1982 | Molloy et al. | 564/347 |

FOREIGN PATENT DOCUMENTS

0380924 A1  8/1990  European Pat. Off.
0391070 A1 10/1990  European Pat. Off.

OTHER PUBLICATIONS

"Synthesis of $^{14}$C- and $^{3}$H-Labeled Fluoxetine, A Selective Serotonin Uptake Inhibitor", Robertson et al., *Journal Compounds and Radiopharmaceuticals*, vol. XXIV, No. 11, pp. 1397–1404, Lilly Research Laboratories, Feb. 1987.

"Chiral Synthesis Via Organoboranes. 18. Selective Reductions. 43. Diisopinocampheylchloroborane as an Excellent Chiral Reducing Reagent for the Synthesis of Halo Alcohols of High Enantiomeric Purity. A Highly Enantioselective Synthesis of Both Optical Isomers of Tomoxetine, Fluoxetine, and Nisoxetine", Srebnik et al., *J. Org. Chem.*, 1988, 53, pp. 2916–2920, 1988.

*Primary Examiner*—Richard L. Raymond
*Attorney, Agent, or Firm*—Oliff & Berridge

[57] ABSTRACT

4-methyl-3-[(4-trifluormethyl)phenoxy]-3-phenyl propylamine (I) is prepared by reacting 3-dimethylamino-1-phenyl-1-propanol (III) with haloformate (VIII) to obtain a substituted propyl carbamate (IX) which is hydrolyzed under basic conditions to yield methylamino-1-phenyl-1-propanol (X). The methylamino-1-phenyl-1-propanol is then converted to fluoxetine (I) by reaction with 4-halobenzotrifluoride (XI).

In the process certain substituted carbamates are obtained as intermediates.

12 Claims, No Drawings

PRODUCTION OF FLUOXETINE AND NEW INTERMEDIATES

FIELD OF THE INVENTION

The present invention relates to a new process for the preparation of N-methyl-3-[(4-trifluoromethyl)phenoxy]-3-phenyl propylamine (fluoxetine), which is also known by the generic name fluoxetine and of its pharmaceutically acceptable acid addition salts as well as to a novel group of intermediates to be used in the above process.

BACKGROUND OF THE INVENTION AND PRIOR ART

Fluoxetine as shown below in Formula I

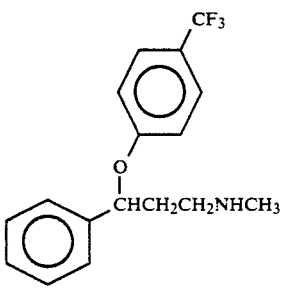

in the form of hydrochloride salt is used as an efficient antidepressant drug. Its pharmacological activity is attributed to its ability to be a potent and selective serotonin re-uptake inhibitor.

Fluoxetine and a process for the preparation of fluoxetine and its pharmaceutically acceptable addition salts were described in U.S. Pat. No. 4,314,081 and U.S. Pat. No. 4,194,004 respectively and U.S. Pat. No. 4,018,895 describes its use in treating depression. In all these patents the same preparation process was described.

In that process 3-dimethylamino propiophenone (formula II) is liberated from its hydrochloride salt and reduced with diborane to yield 3-dimethylamino-1-phenyl-1-propanol (formula III)

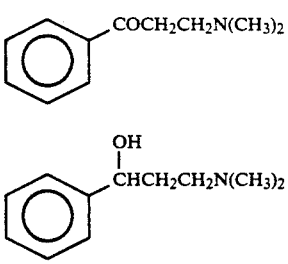

The compound of formula III is treated with HCl and thionyl chloride to yield the chloro derivative (formula IV)

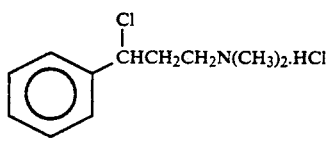

which is then refluxed under alkaline conditions with 4-trifluoromethyl phenol (formula V) for five days

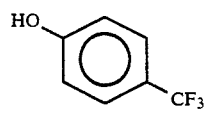

to yield N,N-dimethyl-3-[4-(trifluoromethyl)phenoxy]-3-phenyl propylamine (formula VI)

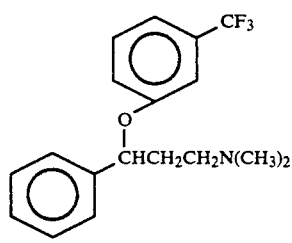

Finally the compound of formula VI is demethylated in a two-step reaction: In a first step the compound is reacted with cyanogen bromide and in a second step with a mixture of KOH/ethylene glycol for 20 hours at 130° C. The crude fluoxetine thus obtained is precipitated as the oxalate or maleate salt.

This process suffers from several disadvantages, the most important of which are:

a) Low overall yields; the yield from compound II to fluoxetine oxalate being only about 32%.
b) The substituted phenol (formula V) which is an essential building block, is not available commercially.
c) The cyanogen bromide which is used in this process is highly toxic.
d) Long time and extreme reaction conditions are required in both the reaction of the compound of formula IV with the compound of formula V and in the demethylation of the compound of formula VI to yield fluoxetine.

Several years later Robertson et al., J. Labelled Compd. Radiopharm., 24, 1997 (1987) described a related process which overcomes some of the above drawbacks. In this process the compound of formula III is directly coupled with the commercially available 4-chlorobenzotrifluoride (formula VII)

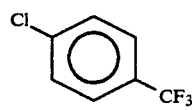

to yield the compound of formula VI. Another change consists in that cyanogen bromide is replaced by the less toxic phenyl chloroformate which, moreover, also reduces the reaction time and temperature of the demethylation of the compound of formula VI.

This process has, however, other disadvantages:

a) The fluoxetine thus obtained is so impure that is has to be purified by preparative HPLC. This is a very costly technique and almost impossible to carry out on a commercial production scale.
b) The process yields phenol in the aqueous waste withdrawn from the demethylation reaction of the compound of formula VI which is a major ecological problem.

Several more processes are described in the literature, but they all suffer from significant drawbacks such as the necessity of catalytic reductions or catalytic dehydrogenations as in the process described, for example, in EP 391,070. EP 380,924 involves a difficult reduction step which is performed using the relatively expensive and dangerous agent (LiAlH$_4$). Another process is described by Srebnik et al. J. Org. Chem., 53, 2916 (1987), but has the disadvantage that it requires high pressure reactions.

SUMMARY OF THE INVENTION

In accordance with the present invention there is provided a process of preparing N-methyl-3-[(4-trifluoro-methyl)phenoxy]-3-phenyl propylamine (fluoxetine) and acid addition salts thereof, comprising preparing 3-dimethylamino-1-phenyl-1-propanol as known per se, characterized in that 3-dimethylamino-1-phenyl-1-propanol is reacted in a suitable solvent with a compound of formula VIII

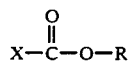
VIII wherein X is halogen and R is an alkyl group to yield, upon neutralization of liberated HX a compound of formula IX

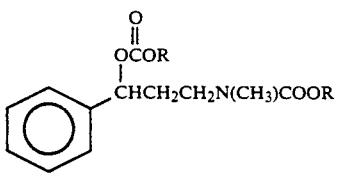
IX wherein R has the same meaning as above, in that the compound of formula IX is hydrolysed under basic conditions to yield a compound of formula X

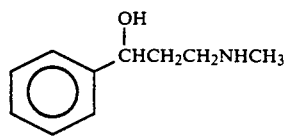
X and in that the compound of formula X is reacted with a compound of formula XI

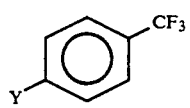
XI wherein Y is a chlorine or fluorine, to yield fluoxetine which, if desired, is converted into an acid addition salt by methods known per se.

DETAILED DESCRIPTION OF THE INVENTION

The new process uses a novel route towards the synthesis of fluoxetine. The process is characterized by the following steps:
Step A The 3-dimethylamino-1-phenyl-1-propanol (described before as compound III) is a readily available material. A possible way to obtain it from 3-dimethylaminopropiophenone hydrochloride is described in U.S. Pat. No. 4,314,081. The compound of formula III is treated with a haloformate of the formula VIII

VIII wherein X is a halogen atom and R is an alkyl group. Example for such a compound is ethyl chloroformate. When the reaction is performed at an elevated temperature and in the presence of an acid acceptor compound which neutralises the acid (HX) formed in the course of the reaction, a compound of formula IX is obtained.

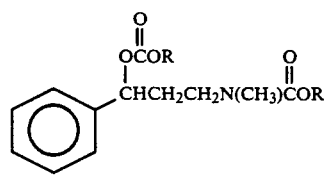
IX

An example for a compound IX is ethyl N-methyl-N-(3-ethoxy-carbonyloxy-3-phenyl)propyl carbamate (formula IX, wherein R=C$_2$H$_5$).

The reaction of compound III with a compound of formula VIII (X and R are as defined before) is a multi-step reaction which is performed in an inert solvent, to yield the compound of formula IX. The reaction is best performed in toluene at reflux whereby water forming in the course of the reaction is continuously distilled off. However lower temperatures (above 80° C.) are also adequate, in which case water will have to be removed at the end of the reaction, e.g. by phase separation. For the reaction to proceed to yield the compound of formula IX the acid HX that forms has to be neutralised. By the preferred mode of operation the reaction is performed in the presence of an acid acceptor such as sodium carbonate, sodium bicarbonate, triethyl amine, sodium hydroxide and the like. Sodium bicarbonate was found to be the most convenient acid acceptor to use.

By another mode of operation no acid acceptor is used in the reaction of compound III with compound VIII, and there is first formed a compound of formula XII

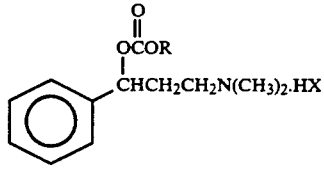
XII which upon neutralization of the acid and the addition of a further amount of the compound of formula VIII is converted into the compounds of formula IX.

Both these modes of operation form part of the present invention.

Theoretically, two equivalents of the compound of formula VIII are needed. It was, however, found that the practical range is 2.5-3.5 equivalents of the compound of formula VIII, the preferred amount being about 3 equivalents.

At the end of the reaction the salts are removed by water wash. Traces of unreacted compounds of formulae III and XII are removed by acid wash and the compound of formula IX is obtained by evaporation of the solvent.

The compounds of formula IX are novel.

Step B

The compound of formula IX so obtained (see Step A) is hydrolyzed under basic conditions. Both carbonate and carbamate groups are eliminated in this step and 3-methylamino-1-phenyl-1-propanol (formula X) is obtained.

Hydrolysis of a compound of formula IX is effected by treatment with a base such as sodium hydroxide. The reaction is easily performed in aqueous alcohols such as, for example, aqueous ethanol, isopropanol and n-butanol. It was surprisingly found that the hydrolysis occurs readily and may, for example, be complete after 3 hours at reflux in aqueous ethanol (82° C.) which contributes to the good yield and purity of the product. For comparison, the compound of formula XIII below where R=Et is stable towards hydrolysis at 130° C. under similar conditions.

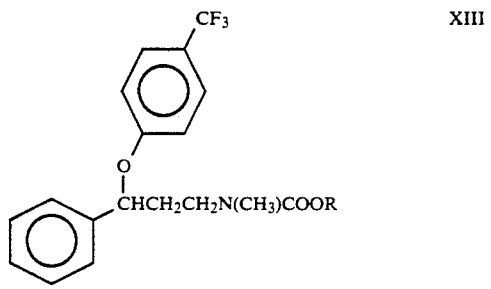

XIII

Against this, in the process according to the invention, the compound of formula IX is hydrolyzed at temperatures below 100° C.

Alternatively, the hydrolysis of a compound of formula IX may be performed as a two-step reaction. In a first step the carbonate is partially hydrolyzed under mild conditions followed by purification, by column chromatography to yield a compound of formula XIV wherein R is an alkyl group.

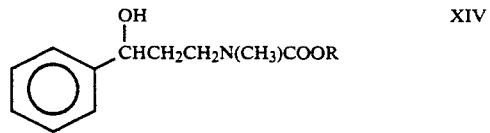

XIV

In a second step the compound of formula XIV is subjected to further hydrolysis to yield the compound of formula X.

Either mode of hydrolysis for the conversion of a compound of formula IX into the compound of formula X is within the scope of the invention.

Step C 3-methylamino-1-phenyl-1-propanol (formula X) is converted to fluoxetine (formula I) using known procedures. Thus, by one procedure the anion formed by reacting compound of formula X with sodium hydride in N,N-dimethylacetamide, is reacted with 4-chlorobenzotrifluoride to give fluoxetine. Optionally, the more expensive 4-fluorobenzotrifluoride can also be used under milder conditions.

Step D

Fluoxetine hydrochloride is isolated by reacting gaseous HCl on a solution of fluoxetine in a suitable solvent such as toluene. The resulting product is collected by filtration.

Other addition salts can also be prepared by known methods.

Step E

The crude fluoxetine hydrochloride is recrystallized in hot water (optionally treated with active charcoal and filtered while hot) and the solution cooled. Pure fluoxetine hydrochloride precipitates and is collected by filtration.

This mode of purification by recrystallization is superior to known procedures such as precipitation from ether (UK 2,060,618) or recrystallization from the toxic acetonitrile (Sharpless, J. Org. Chem. 53, 9081 (1988)).

The advantages achieved by the process of the present invention may be briefly summed up as follows:

1. Good yields are obtained (from II to fluoxetine hydrochloride-66% based on compound II), which are superior to yields obtained by any known processes.
2. High purity fluoxetine hydrochloride is obtained.
3. Considerably less toxic reagents are used in the process.
4. Practically no ecological problems arise (especially if one uses compound VIII where R is an alkyl group or a haloalkyl group).
5. Milder reaction conditions are employed in the process.

The invention is further illustrated by the following Examples to which it is not limited.

EXAMPLE 1

A solution of 3-dimethylamino-1-phenyl-1-propanol (50 g) in toluene (400 ml) was heated to reflux. Ethyl chloroformate (39 g) was added gradually during 90 minutes. The mixture was boiled for another 90 minutes, cooled and filtered. N,N-dimethyl-3-ethoxy-carbonyloxy-3-phenylpropylamine hydrochloride (XII) (70.5 g) was collected and dried. Yield 85.6%.

Mass spectrum: m/e=251 (conforms with structure)
NMR: 1.28 ppm, t, 3H, OCH$_2$CH$_3$; 2.48 ppm, m, 2H, CH—CH$_2$ 2.80 ppm, s, 6H, N—(CH$_3$)$_2$; 3.10 ppm, m, 2H, —CH—CH$_2$—CH$_2$—N 4.15 ppm, m, 2H, OCH$_2$CH$_3$; 5.69 ppm, dd, 1H, PhCH—CH$_2$ 7.35 ppm, m, 5H, Ph.

EXAMPLE 2

A mixture of 3-dimethylamino-1-phenyl-1-propanol (37.1 g), sodium bicarbonate (20.8 g) and toluene (150 ml) was brought to reflux. A Dean Stark azeotropic trap was used to remove the water formed during the reaction. Ethyl chloroformate (67.4 g) was added slowly dropwise during 3.25 hours. The mixture was boiled for another 1.5 hours and cooled to room temperature. Water (100 ml) was added and the mixture was stirred to dissolve all the solids. The phases were separated. The organic phase was washed with a mixture of water (80 ml) and 32% HCl (20 ml). Phases were separated and the organic layer was washed again with water (100 ml). The organic solution was dried over anhydrous magnesium sulfate and filtered. The toluene was evaporated to give 70 g oil. The oil was assayed by HPLC to contain 80.3% of ethyl-N-methyl-N-(3-ethoxy-carbonyloxy-3-phenyl)-propyl carbamate. (Compound IX wherein R=Et). Yield 88%. This oil is suitable for the next step. Pure samples were obtained by high vacuum drying.

Mass spectrum: m/e=309 (conforms with structure)
NMR: 1.25 ppm, m, 6H, OCH$_2$CH$_3$; 2.18 ppm, m, 2H, CH—CH$_2$—CH$_2$ 2.86 ppm, s, 3H, N—CH$_3$; 3.32 ppm, m, 2H, CH—CH$_2$—CH$_2$ 4.14 ppm, m, 4H, OCH$_2$CH$_3$; 5.56 ppm, dd, 1H, PhCH—CH$_2$ 7.35 ppm, m, 5H, Ph,

EXAMPLE 3

MethylN-methyl-N(3-methoxycarbonyloxy-3-phenyl)propyl carbamate (compound IX wherein R=methyl) was prepared in 49% yield, according to Example 2 using methyl chloroformate instead of ethyl chloroformate.

Mass spectrum: m/e=281 (conforms with structure)
NMR: 2.0-2.2 ppm, m, 2H, CH—CH$_2$—CH$_2$; 2.90 ppm, s(broad), 3H, N—CH$_3$; 3.2-3.4 ppm, m, 2H, CH—CH$_2$—CH$_2$; 3.66 ppm, s, 3H, NCOOCH$_3$; 3.74 ppm, s, 3H, OCOOCH$_3$; 5.54 ppm, m, 1H, PhCH; 7.34 ppm, m, 5H, Ph

EXAMPLE 4

Isobutyl N-methyl-N-(3-isobutoxycarbonyloxy-3-phenyl) propyl carbamate (compound IX wherein R=isobutyl) was prepared in 72% yield, according to Example 2 using isobutyl chloroformate instead of ethyl chloroformate.

Mass spectrum: m/e=365 (conforms with structure)
NMR: 0.91 ppm, d+d, 12H, CH$_2$—CH—(CH$_3$)$_2$; 1.90 ppm, m, 2H, CH2—CH—(CH$_3$)$_2$; 2.15 ppm, m, 2H, CH—CH$_2$—CH$_2$; 2.89 ppm, s, 3H, N—CH3; 3.32 ppm, m, 2H, CH—CH$_2$—CH$_2$; 3.90 ppm, m, 4H, COO—CH$_2$; 5.41 ppm, dd, 1H, Ph—CH; 7.3 ppm, m, 5H, Ph,

EXAMPLE 5

Isopropyl N-methyl-N-(3-isopropoxycarbonyloxy-3-phenyl) propyl carbamate (compound IX where R=isopropyl) was prepared in 95% yield, according to Example 2 using isopropyl chloroformate instead of ethyl chloroformate.

Mass spectrum: m/e=337 (conforms with structure),
NMR: 1.24,1.29 ppm, d+d, 12H, CH—(CH$_3$)$_2$; 2.0-2.2 ppm, m, 2H, CH—CH$_2$—CH$_2$; 2.85 ppm, s, 3H, N—CH$_3$; 3.3 ppm, m(broad), 2H, CH—CH$_2$—CH$_2$; 4.85 ppm, m, 2H, COOCH(CH$_3$)$_2$; 5.54 ppm, dd, 1H, Ph—CH; 7.45 ppm, m, 5H, Ph,

EXAMPLE 6

N,N-dimethyl-3-ethoxycarbonyloxy-3-phenyl-propylam-ine hydrochloride (XII) (21.3 g) was dissolved in water (100 ml). Toluene (100 ml) was added. The pH was adjusted to 13 using NaOH and the free base was extracted to the toluene phase. After phase separation toluene (50 ml) was added and the solution was dried by an azeotropic distillation using a Dean Stark trap.Ethyl chloroformate (29 g) was added slowly. The mixture was boiled for 3 hours and cooled. The solvent was evaporated under reduced pressure to give 29.4 g oil which was shown by HPLC to contain 82.5% of compound IX (R=Et).
Yield 92.4%.

EXAMPLE 7

Compound IX (R=Et) (310.3 g) was mixed with water (1500 ml) and ethanol (500 ml). Solid sodium hydroxide (340 g) was added and the mixture was boiled for 3 hours (ca. 82° C.). The phases were separated and the ethanol evaporated to give 157 g of 3-methylamino-1-phenyl-1-propanol (X) as an oil which solidified on standing.
Yield 94.8%.

EXAMPLE 8

Compound IX (R=Et) (115 g) was added to a solution of NaOH (130 g) in water (450 ml) and n-butanol (450 ml). The mixture was boiled for 3 hours and cooled. The phases were separated. The organic solvent was thoroughly evaporated to give 55 g of 3-methylamino-1-phenyl-1-propanol (X). Yield 89.6%.

EXAMPLE 9

Compound IX(R=Et) (43.2 g, 87.4% assay) was mixed with water (195 ml), isopropanol (65 ml) and sodium hydroxide (34.2 g). The mixture was boiled under reflux for 6 hours and cooled to 40° C. The phases were separated, the upper organic phase (120.5 g) was shown to contain 16.1% of (i.e. 19.4 g) of 3-methylamino-1-phenyl-1-propanol (X), which was sufficiently pure for the next step. It can be directly used for the next step after removing the isopropanol by distillation.
Yield 96.4%.

EXAMPLES 10-12

Under similar conditions to those given in Example 9 the following compounds of formula IX were hydrolyzed to give 3-methylamino-1-phenyl propanol (X). The time of reaction and yields are given in the table:

| R in IX | Time (hrs.) | Yield (%) |
| --- | --- | --- |
| i-Pr | 28 | 77 |
| i-Bu | 14 | 65 |
| Me | 3 | 85 |

EXAMPLE 13

Compound IX(R=Et) (20.5 g) was mixed with water (112.5 ml) and ethanol (37.5 ml). Slowly, while keeping the temperature below 25° C., solid NaOH (12.1 g) was added. After mixing for 24 hours at 25° C. the phases were separated. The lower layer was evaporated from ethanol and extracted with toluene. The combined organic layers were washed with a mixture of water (24 ml) and 32% HCl (6 ml). After phase separation the organic solvents were removed. An oil (14.5 ) was obtained. The oil was purified by column chromatography (hexane:ethyl acetate 6:4). The product N-carbethoxy-N-methyl-3-phenyl-3-hydroxy propylamine (compound of formula XIV; R=Et) was obtained as an oil (7.6 g).
Yield 48%.

Mass spectrum: m/e=237 (conforms with structure).

EXAMPLE 14

Preparation of fluoxetine hydrochloride

A mixture of dimethylacetamide (70 ml), toluene (20 ml), 4-chlorobenzotrifluoride (15 ml) and 3-methylamino-1-phenyl-1-propanol (15.6 ml) was heated to 115° C. A suspension of sodium hydride (6.2 g) in toluene (20 ml) was added gradually. The mixture was kept at 115° C. for 1 hour and cooled. Water (160 ml) and toluene (160 ml) were added. The phases were separated. The dried toluene phase was treated, with cooling, with gaseous hydrogen chloride. Fluoxetine hydrochloride (27.6 g) was precipitated. It was filtered and dried.

Yield 86%.

EXAMPLE 15

Crude fluoxetine hydrochloride (55 g, prepared as described in the reference example) was added to water (155 ml). The mixture was heated to ca. 60° C. and a homogeneous solution was obtained. Active charcoal (2.75 g) was added and the mixture was stirred for 30 minutes at ca. 60° C. The mixture was filtered and the solution was gradually cooled to 10° C. and stirred at that temperature for another hour. The product was filtered, washed with water (50 ml) and dried to give pure fluoxetine hydrochloride (46.8 g).

Yield 85.1%; m.p. 156.5°–157° C.

We claim:

1. A process of preparing N-methyl-3-[(4-trifluoromethyl)phenoxy]-3-phenyl propylamine (fluoxetine) and acid addition salts thereof, comprising preparing 3-dimethylamino-1-phenyl-1-propanol as known per se, characterized in that 3-dimethylamino-1-phenyl-1-propanol (III) is reacted in a suitable solvent with a compound of formula VIII

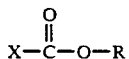

VIII wherein X is halogen and R is an alkyl group to yield, upon neutralization of liberated HX, a compound of formula IX

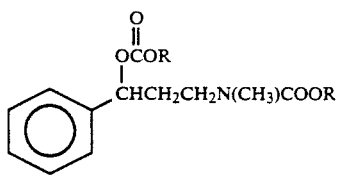

IX wherein R has the same meaning as above, the compound of formula IX is hydrolized under basic conditions to yield a compound of formula X

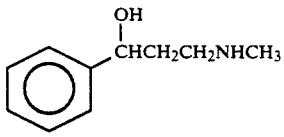

X and the compound of formula X is reacted with a compound of formula XI

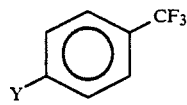

XI wherein Y is a chlorine or fluorine atom, to yield fluoxetine which compound XI is, if desired, converted into an acid addition salt by methods known per se.

2. A process as claimed in claim 1, wherein in formula VIII X is chlorine and R is ethyl.

3. A process as claimed in claim 1, wherein in formula VIII X is chlorine and R is methyl, isopropyl or isobutyl.

4. A process as claimed in claim 1, wherein the reaction between the compounds of formulae III and VIII is performed in toluene.

5. A process as claimed in claim 4, wherein the reaction is carried out under reflux.

6. A process as claimed in claim 1, wherein the reaction between the compounds of formulae III and VIII is performed in the presence of an acid acceptor.

7. A process as claimed in claim 6, wherein the acid acceptor is selected from the group consisting of sodium bicarbonate, sodium carbonate, triethylamine and sodium hydroxide.

8. A process as claimed in claim 1, wherein the reaction between the compounds of formulae III and VIII is carried out in two stages and an acid acceptor is added at the second stage together with a further amount of the compound of formula VIII.

9. A process as claimed in claim 1, wherein the hydrolysis of said compound IX is effected in aqueous isopropanol.

10. A substituted propyl carbamate of the formula

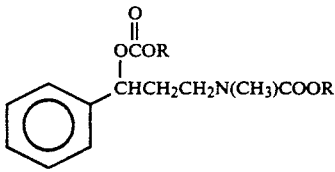

IX wherein R has the same meaning as in claim 1.

11. The compound of claim 10 in which R is ethyl.

12. The compound of claim 10 in which R is methyl, isopropyl or isobutyl.

* * * * *